US006169195B1

(12) United States Patent
Schinabeck et al.

(10) Patent No.: US 6,169,195 B1
(45) Date of Patent: Jan. 2, 2001

(54) PROCESS FOR THE REMOVAL OF CHLOROHYDROCARBONS FROM ORGANOCHLOROSILANES

(75) Inventors: Anton Schinabeck, Burghausen; Konrad Mautner, Nünchritz, both of (DE)

(73) Assignee: Wacker-Chemie GmbH, Munich (DE)

( * ) Notice: Under 35 U.S.C. 154(b), the term of this patent shall be extended for 0 days.

(21) Appl. No.: 09/484,978

(22) Filed: Jan. 18, 2000

(30) Foreign Application Priority Data

Jan. 21, 1999 (DE) .............................. 199 02 270

(51) Int. Cl.$^7$ ........................................ C07F 7/08
(52) U.S. Cl. ............................ 556/466; 556/472
(58) Field of Search ..................... 556/466, 472

(56) References Cited

U.S. PATENT DOCUMENTS

| 4,127,598 | 11/1978 | McEntee . | |
|---|---|---|---|
| 4,661,612 | * 4/1987 | George et al. | 556/466 X |
| 4,774,347 | 9/1988 | Marko et al. . | |
| 4,962,221 | * 10/1990 | Huntress et al. | 556/466 X |
| 5,777,145 | 7/1998 | Marko . | |

OTHER PUBLICATIONS

International Search Report—Apr. 19, 2000.
"Chemie Ingenieur Technik 69", pp. 283–290, Mar. 1997.
"Materials and Corrosion" (Jun. 1997), pp. 542–548.

* cited by examiner

Primary Examiner—Paul F. Shaver
(74) Attorney, Agent, or Firm—Brooks & Kushman P.C.

(57) ABSTRACT

The invention relates to a process for cleavage of chlorohydrocarbons which are present as an impurity in organochlorosilanes, in which the chlorohydrocarbons are brought into contact with steel surfaces which comprise nickel as an alloying constituent, and are cleaved into olefins and hydrogen chloride.

12 Claims, No Drawings

PROCESS FOR THE REMOVAL OF CHLOROHYDROCARBONS FROM ORGANOCHLOROSILANES

TECHNICAL FIELD

The invention relates to a process for purifying organochlorosilanes by cleavage of chlorohydrocarbons which are present as an impurity in the commercial production of crude organochlorosilanes.

BACKGROUND ART

Chlorohydrocarbons are formed as secondary constituents of Müller-Rochow organochlorosilanes synthesis. During separation of the organochlorosilanes by distillation, the chlorohydrocarbons will appear in the various silane fractions according to their boiling range. Chlorohydrocarbons lead to a number of disadvantages, in particular during and after processing of organochlorosilanes to secondary products.

Processes have therefore been developed which separate chlorohydrocarbons from organochlorosilanes. U.S. Pat. No. 4,127,598 describes a process in which chlorohydrocarbons are adsorbed onto active charcoal or molecular sieves. The reduction of chlorohydrocarbons to the corresponding alkanes with hydrogencontaining silanes on aluminum oxide is described in U.S. Pat. No. 4,774,347, and reduction on aluminum oxide-zirconium oxide co-gels is described in U.S. Pat. No. 5,777,145. The preserve of the alkanes thus formed cause no trouble because of their low reactivity. Moreover, the alkanes can usually be separated easily by distillation because of the changed boiling point.

DISCLOSURE OF INVENTION

The invention relates to a process for cleavage of chlorohydrocarbons which are present as an impurity in organochlorosilanes, in which the chlorohydrocarbons are brought into contact with steel surfaces which comprise nickel as an alloying constituent and are cleaved thereby into olefins and hydrogen chloride.

BEST MODE FOR CARRYING OUT THE INVENTION

The organochlorosilanes have the general formula 1

$$R_a SiCl_{4-a}, \quad (1)$$

in which:
R are identical or different substituents which are chosen from hydrogen, linear or branched alkyl radicals having 1 to 6 carbon atoms or aryl radicals having 6 to 9 carbon atoms and
a is 0, 1, 2, 3 or 4.
In the preferred organochlorosilanes of the general formula 1, R is a methyl or phenyl radical.

During the preparation of organochlorosilanes, by-products which are formed are, inter alia, chlorohydrocarbons which, in particular, have the general formula R'-Cl, in which R' is an alkyl radical or alkaryl radical having 3 to 20 carbon atoms. The preferred radicals R' are linear or branched alkyl radicals having 4 to 7 carbon atoms, for example iso-butyl, iso-pentyl, iso-hexyl, 2,3-dimethylbut-2-yl, 3-methylpent-2-yl and 2,3,3-trimethylbut-2-yl. The content of chlorohydrocarbons in the organochlorosilane mixtures is usually 1 ppm to 5000 ppm.

The chlorohydrocarbons eliminate hydrogen chloride on steel surfaces formulated to have a catalytic action, and are converted into olefins. Preferably, in a first embodiment, the steels comprise at least 4% by weight of nickel, in particular 5–70% by weight, a chromium content of at least 10% by weight, in particular at least 16% by weight, and 0 to 20% by weight of molybdenum, preferably 2 to 7% by weight or 13–16% by weight. In a second embodiment, the steels have a nickel content of at least 50% by weight, in particular at least 65% by weight, and a molybdenum content of at least 20% by weight, in particular 25 to 35% by weight. Steels which comprise a chromium content of at least 10% by weight, in particular at least 16% by weight, and at least 5% by weight, in particular at least 5 to 31% by weight of nickel are preferred.

High-grade steel s are preferred. High-grade steels which can be employed are chromium-, nickel- and optionally molybdenum-containing steels (chro-steels), for example standard austenitic steels with 18% of Cr and 10% of Ni or 17% of Cr, 12% of Ni and 2% of Mo, duplex steels with 22% of Cr, 5% of Ni and 3% of Mo or 25% of Cr, 7% of Ni and 4% of Mo, and special austenitic steels with 20–33% of Cr, 18–31% of Ni and 2–7% of Mo, such as are described, for example, in Heinke, G.; Korkhaus, J.; Chemie Ingenieur Technik 69, 283–290. However, high-grade steels of the Ni-Cr-Mo alloy such as are described in Agarwal, D. C.; Herda, W. R.; Materials and Corrosion, 48, 542–548 (1997) can also be employed.

In addition to iron and the alloying constituents mentioned, further elements can also be alloyed in; for example, but not by way of limitation, titanium, copper and niobium. Austenitic steels and duplex steels are preferred.

Examples of the high-grade steels mentioned are materials with the material number 1.4571, 1.4404 and SS316 (17% of Cr, 12% of Ni, in each case 2% of a different alloy) or Hastelloy B2 (72% of Ni, 28% of Cr).

The cleavage of the chlorohydrocarbons increases with an increasing rate as the temperature increases. Cleavage is preferably carried out at 0° C. to 150° C., in particular 70 to 110° C. The residence time can be 1 minute to 10 hours, and is preferably 1 to 5 hours. The pressure is preferably 1 to 2 bar, but lower or higher pressures are also possible.

The steel surfaces can be made available in a suitable geometry, for example in gauzes and in separate reactors. However, they can also be steel baffles of sufficient surface area in apparatuses, such as, for example, distillation columns The cleavage efficiencies for the chlorohydrocarbons are typically above 90%. The olefins formed can be removed by distillation, since the boiling points of the olefins and of the corresponding chlorohydrocarbons and therefore also of the chlorosilane or chlorosilane mixture in which the chlorohydrocarbon was concentrated on the basis of its boiling point are sufficiently far apart.

In the examples described below, all the parts and percentages data relate to the weight, unless stated otherwise. Unless stated otherwise, the examples below were carried out under a pressure of the surrounding atmosphere, that is to say about 1000 hPa.

EXAMPLES

Example 1 (Comparison Example)

A mixture containing 45.1% by weight of methyltrichlorosilane and 54.2% by weight of dimethyldichlorosilane was distilled in a perforated tray column of 1.4 m diameter and with 150 trays of commercially available, non-alloyed HII steel. The contamination with chlorohydrocarbons comprised 550 ppm of 2-chloro-2,3-dimethylbutane, 325 ppm of 2-chloro-2-methylpentane and 190 ppm of 2-chloro-3-methylpentane. The remainder comprised saturated hydrocarbons, chiefly 2,2,3-trimethylbutane. The top product, methyltrichlorosilane with <1% of dimethyldichlorosilane, contained <50 ppm of the corresponding olefins. The chlorohydrocarbons were discharged in the bottom product, dimethyldichlorosilane with 5% of methyldichlorosilane.

Example 2

A mixture which comprised 70.9% by weight of methyltrichlorosilane and 28.5% by weight of dimethyldichlorosilane was distilled in a column of 1.7 m diameter with 150 valve trays with high-grade steel valves of material 1.4571. The contamination with chlorohydrocarbons comprised 610 ppm of 2-chloro-2,3-dimethylbutane, 347 ppm of 2-chloro-2-methylpentane and 308 ppm of 2-chloro-3-methylpentane. The remainder comprised saturated hydrocarbons, again chiefly 2,2,3-trimethylbutane. The top product, methyltrichlorosilane with <1% of dimethyldichlorosilane, contained 790 ppm of the corresponding olefins 2,3-dimethyl-2-butene, 2-methyl-2-pentene and 3-methyl-2-pentene. The <50 ppm of chlorohydrocarbons were discharged in the bottom product, dimethyldichlorosilane with 5% of methyldichlorosilane.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for cleavage of chlorohydrocarbons which are present as an impurity in the commercial production of organochlorosilanes, comprising contacting said chlorohydrocarbons with surfaces which comprise nickel-alloyed steel, and cleaving said chlorohydrocarbons into olefins and hydrogen chloride.

2. The process as claimed in claim 1, in which the chlorohydrocarbons have the general formula R'—Cl, in which R' is an alkyl radical or alkaryl radical having 3 to 20 carbon atoms.

3. The process as claimed in claim 1, in which the nickel-alloyed steel has a nickel content of at least 5% by weight.

4. The process as claimed in claim 1, in which the nickel-alloyed steel has a chromium content of at least 10% by weight.

5. A process for the purification of a crude organochlorosilane mixture produced by the Müller-Rochow process, said crude organochlorosilanes containing chlorohydrocarbons as an impurity, said process comprising contacting said crude organochlorosilane mixture with a nickel-containing steel at a temperature of 0° C. to 150° C., the surface area of said nickel-containing steel sufficient to cleave a major portion of said chlorohydrocarbons into alkene and hydrogen chloride within a period of five hours, and separating the alkenes formed from an organochlorosilane product by distillation.

6. The process of claim 5, wherein said nickel-containing steel is an alloy comprising, in addition to iron, in weight percent, 4–70% nickel, 10% or more chromium, and 2–16% molybdenum.

7. The process of claim 5, wherein said nickel-containing steel is an alloy comprising, in addition to iron, in weight percent, >50% Ni, and >20% Mo.

8. The process of claim 5, wherein said nickel-containing steel is an alloy comprising, in addition to iron, in weight percent, about 12% Ni, about 17% Cr, and about 2% Mo.

9. The process of claim 5, wherein said nickel-containing steel is an alloy comprising, in addition to iron, in weight percent, about 5% Ni, about 22% Cr, and about 3% Mo.

10. The process of claim 5, wherein said nickel-containing steel is an alloy comprising, in addition to iron, in weight percent, 18–31% Ni, 20–33% Cr, 2–7% Mo.

11. The process of claim 5, wherein said nickel-containing steel is an alloy comprising, in addition to iron, in weight percent, about 12% Ni, and about 17% Cr.

12. The process of claim 5, wherein said nickel-containing steel comprises distillation column trays, baffles, valves, filling material, or packing.

* * * * *